United States Patent [19]
Benton et al.

[11] 3,940,804
[45] Mar. 2, 1976

[54] ANKLE BLOCK

[75] Inventors: Cecil Thomas Benton, Saratoga; John Maher Freter, Santa Clara; Robert R. Moore, Hayward, all of Calif.

[73] Assignee: Hosmer/Dorrance Corporation, Campbell, Calif.

[22] Filed: Mar. 10, 1975

[21] Appl. No.: 557,018

[52] U.S. Cl. .................................. 3/30; 3/7; 3/33
[51] Int. Cl.² ...................... A61F 1/04; A61F 1/08
[58] Field of Search ........................... 3/30–35, 6–7, 3/1, 2, 21

[56] References Cited
UNITED STATES PATENTS

| | | | |
|---|---|---|---|
| 3,098,239 | 7/1963 | Nader | 3/7 |
| 3,440,668 | 4/1969 | Dachs et al. | 3/1 |
| 3,551,915 | 1/1971 | Woodall | 3/21 |

FOREIGN PATENTS OR APPLICATIONS

| | | | |
|---|---|---|---|
| 1,179,328 | 10/1964 | Germany | 3/34 |

*Primary Examiner*—Ronald L. Frinks
*Attorney, Agent, or Firm*—Harris Zimmerman

[57] ABSTRACT

An ankle block for joining a leg prosthesis to a foot prosthesis includes a generally cylindrical member formed of rigid foam material, and a metal or wood insert molded in place in the lower end of the cylindrical member. The insert includes flanges which anchor it firmly in the foam, and a hole extending axially therethrough for receiving and anchoring a bolt from the prosthetic foot. An upper cylindrical passage extends from the upper end of the block to the insert, and a lower cylindrical passage of smaller diameter extends likewise from the lower end. The insert is adapted to receive and anchor either a bolt from a Sach foot, or a tee-bolt from a single-axis foot prosthesis.

2 Claims, 2 Drawing Figures

U.S. Patent   March 2, 1976   3,940,804
FIG_1
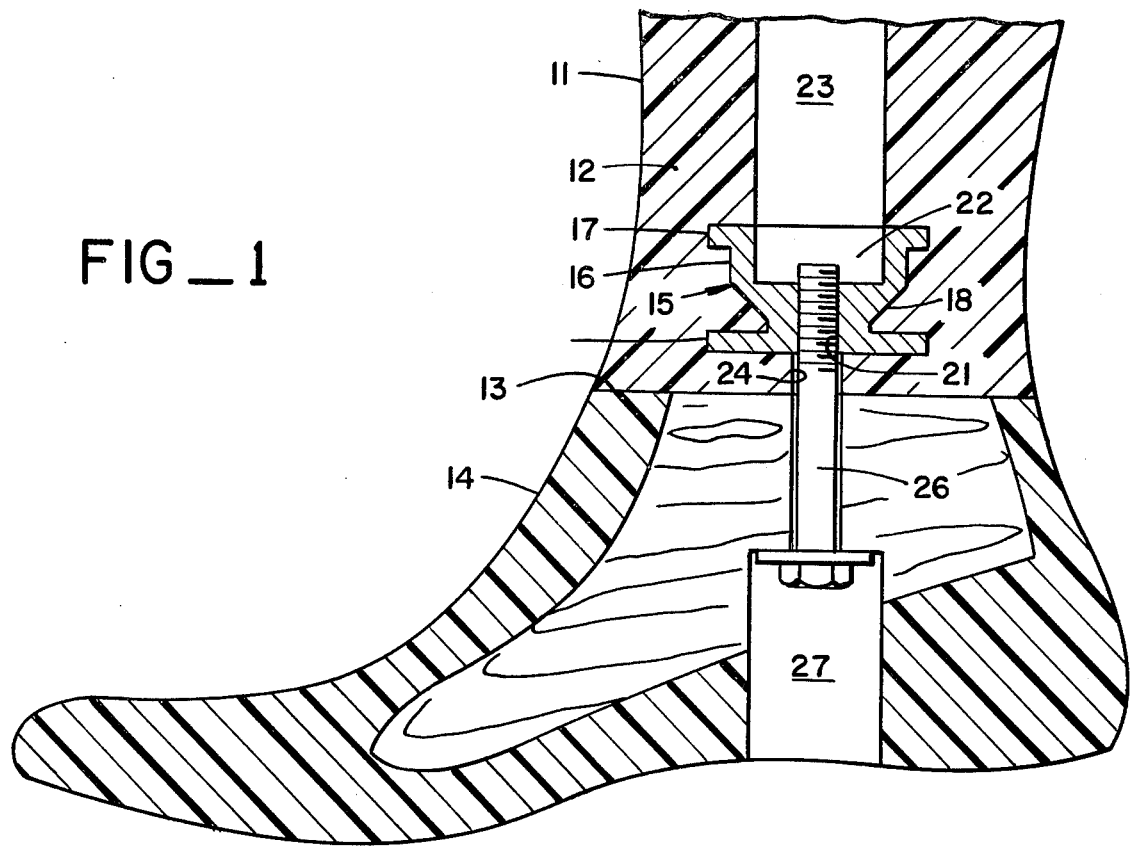
FIG_2
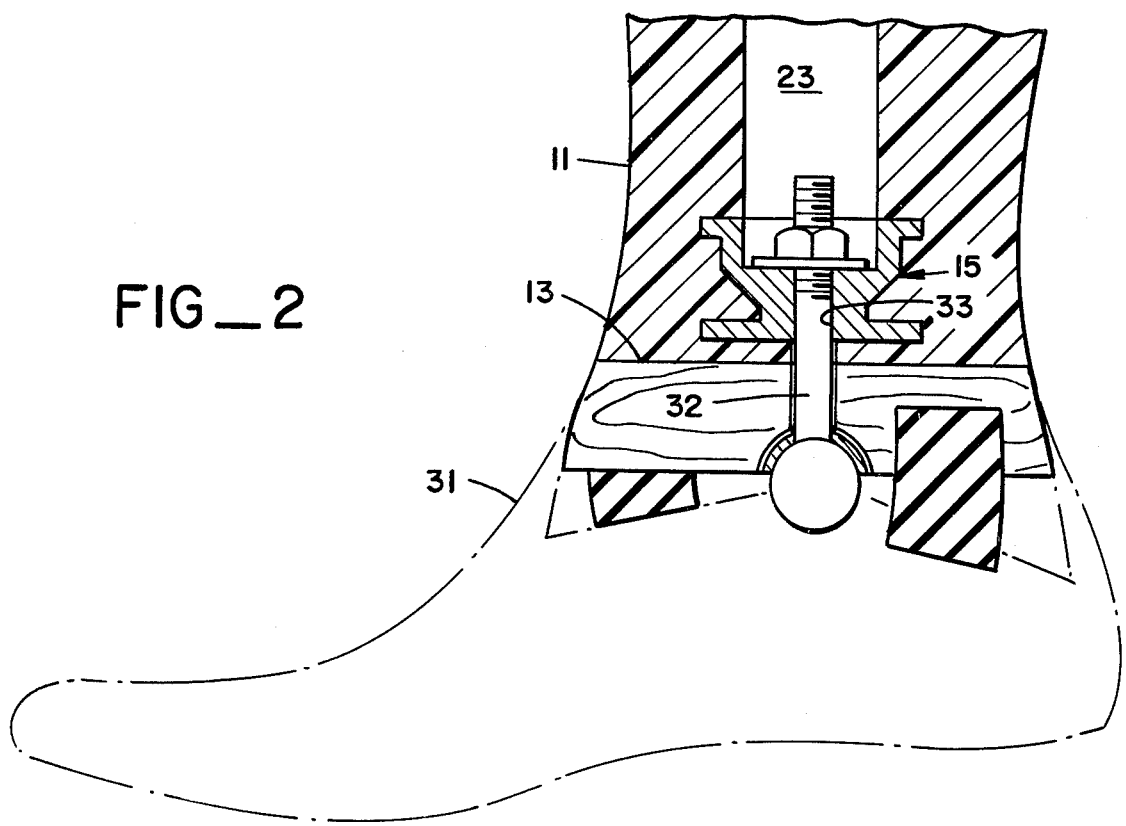

ANKLE BLOCK

BACKGROUND OF THE INVENTION

An ankle block is a device known in the prosthetic art for its use in joining a foot prosthesis to a leg prosthesis. Generally speaking, prior art ankle blocks are formed of wood, metal, or the like, and include a means for bolting the foot prosthesis thereto. Such means usually include a plate or the like embedded in the ankle block for receiving the foot bolt. Such a plate requires expensive machining to be emplaced properly in the ankle block, since access holes to the top and bottom of the plate are required, and must be bored or drilled out as needed. These procedures add significantly to the cost of the ankle block. It should also be noted that the materials for fabricating the ankle block are chosen for strength, rigidity, light weight, and their ability to be formed to resemble the human ankle. In the case of metal or wood, the labor required to achieve the proper form also increases the total cost of the ankle block.

SUMMARY OF THE INVENTION

The present invention generally comprises an ankle block which is molded of rigid foam material such as polyurethane, and which is formed in one step with the desired exterior shape. In the molding process, an insert adapted to receive and secure a bolt extending from the prosthetic foot is molded in place within the block, as are the required access holes extending to the insert. Thus much of the labor required to fabricate the ankle blocks of the prior art is eliminated, as is a significant amount of weight.

The insert itself comprises a unitary metal, or wood, or high impact plastic member, preferably having a cylindrical upper portion, an inwardly tapering medial portion, and a lower portion comprising an outwardly directed flange. The upper portion is also provided with a flange equal in diameter to its counterpart, both flanges aiding in anchoring the insert securely in the rigid foam. A bolt hole extends axially through the insert, and is provided with a counterbore at the upper end thereof. The bolt hole may be threaded or smooth, as required by the foot prosthesis connecting means.

THE DRAWING

FIG. 1 is a cross-sectional elevation of one embodiment of the present invention.

FIG. 2 is a cross-sectional elevation of a further embodiment of the present invention.

DESCRIPTION OF THE PREFERRED EMBODIMENT

The present invention generally constitutes an ankle block typically employed in joining a prosthetic leg to a prosthetic foot. With reference to FIG. 1, the ankle block includes a generally cylindrical member 11 tapered and contoured to resemble a human ankle. The member 11 is cast of rigid foam material 12 such as polyurethane or the like, and includes a planar lower surface 13 normal to the axis of the member 11. The upper end of the member 11 is provided with means for joining the ankle block to the leg prosthesis, such means being commonly known in the art and not germane to the present invention. The lower surface 13 abuts the prosthetic foot 14, a Sach foot which forms no independent part of the present invention.

Cast within the member 11 is an anchoring insert 15. As here illustrated, the unitary insert 15 includes a cylindrical upper portion 16 from which extends an upper flange 17, and a downwardly tapering medial portion 18 depending subjacently from the upper portion 16. Extending from the lower end of the portion 18 is an outwardly directed lower flange 19 approximately equal in diameter to its upper counterpart. A threaded hole 21 extends coaxially with the axis of the insert and the member 11, and is provided with a counterbore 22 at the upper end thereof. The shape of the insert and the flanges extending therefrom are designed to securely anchor the insert in the foam without undue stress.

Extending downwardly from the upper end of the ankle block is an upper access passage 23, equal in diameter to the counterbore, and extending axially in the member 11. A lower access passage 24 extends axially from the surface 13 to the threaded hole 24, and is slightly larger in diameter than the latter. The lower access passage permits an anchoring bolt 26 extending from the Sach foot 14 to reach and engage the threaded hole 24, thereby to anchor the foot to the block. The bolt 26 is rotated by means of the access port 27 in the Sach foot.

It should be noted that the ankle block is cast of selfcuring foam material, and that all of its salient features are formed in the casting process. The external shape is provided by the casting mold, and mold inserts form the passages 23 and 24. Furthermore, the anchoring insert is held in its proper place by the mold inserts during the poruing and curing process, so that virtually the entire ankle block is created in this one process. Those individuals skilled in the prosthetic art may appreciate the simplicity and integrity of this construction as opposed to prior art devices. The outer surface of the ankle block may be shaped to anatomical configuration and provided with an exterior surface laminate pigmented to match the skin tones of the wearer.

The ankle block of the present invention is also adapted to receive and anchor a tee-bolt 32 which is typically used to secure a single axis foot prosthesis 31 to the ankle block, as depicted in FIG. 2. In this instance it is not appropriate to provide a threaded hole in the anchoring insert 15 as the tee-bolt can only be rotated by rotating the prosthetic foot, an unwieldy process at least, which can misalign the foot. Rather, a smooth bore 33 is provided through the anchoring insert, and access is had through the passage 23 to the top of the insert to secure a nut 34 in the counterbore 22 to the tee-bolt. Tightening the nut 34 on the bolt 32 secures the foot to the ankle block.

It should be noted that the insert 15 may initially be provided with a smooth bore for the tee-bolt. Alternatively, an existing threaded hole 24 as shown in FIG. 1 may be drilled out to create a smooth bore 33 when required. Also, in the embodiment of FIG. 2, the lower surface 13 may require trimming so that a requisite length of the threaded portion of the tee-bolt extends into the counterbore to engage the nut.

We claim:

1. A prosthetic ankle block comprising a generally cylindrical member contoured to resemble a human ankle and cast of rigid foam material, including an anchoring insert imbedded in said foam material for anchoring a prosthetic foot to said ankle block; said insert including an upper cylindrical portion having an upper flange extending radially outwardly therefrom into said foam material, a medial portion comprising a frusto-conical member integrally formed with and subjacent to said upper portion, and a lower flange extending radially outwardly from the lower, narrow end of the medial portion; said insert including a hole extending axially therethrough and a counterbore extending into the end surface of the upper portion thereof; and said ankle block including an upper passage communicating with said counterbore and a lower passage extending to the lower opening of said hole.

2. The prosthetic ankle block of claim 1, wherein said hole in said insert is threaded to receive an anchoring bolt of a prosthetic foot.

* * * * *